United States Patent
Takahashi et al.

(10) Patent No.: US 11,399,699 B2
(45) Date of Patent: Aug. 2, 2022

(54) ENDOSCOPE INCLUDING GREEN LIGHT SENSOR WITH LARGER PIXEL NUMBER THAN PIXEL NUMBER OF RED AND BLUE LIGHT SENSORS

(71) Applicant: Sony Corporation, Tokyo (JP)

(72) Inventors: Yasuaki Takahashi, Kanagawa (JP); Kenji Takahashi, Kanagawa (JP); Takeshi Miyai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 102 days.

(21) Appl. No.: 16/611,851

(22) PCT Filed: May 1, 2018

(86) PCT No.: PCT/JP2018/017380
§ 371 (c)(1),
(2) Date: Nov. 7, 2019

(87) PCT Pub. No.: WO2018/211970
PCT Pub. Date: Nov. 22, 2018

(65) Prior Publication Data
US 2020/0214539 A1  Jul. 9, 2020

(30) Foreign Application Priority Data

May 15, 2017 (JP) .............................. JP2017-096200

(51) Int. Cl.
*A61B 1/00* (2006.01)
*A61B 1/045* (2006.01)
(Continued)

(52) U.S. Cl.
CPC ........ *A61B 1/00009* (2013.01); *A61B 1/0005* (2013.01); *A61B 1/00006* (2013.01);
(Continued)

(58) Field of Classification Search
None
See application file for complete search history.

(56) References Cited

U.S. PATENT DOCUMENTS 8,784,301 B2 * 7/2014 McDowall ......... G02B 23/2415
600/109
2004/0245350 A1   12/2004 Zeng
(Continued)

FOREIGN PATENT DOCUMENTS

JP    2008-136732 A    6/2008
JP    2012-170639 A    9/2012
(Continued)

OTHER PUBLICATIONS

International Search Report and Written Opinion dated Jul. 3, 2018 for PCT/JP2018/017380 filed on May 1, 2018, 7 pages including English Translation of the International Search Report.
(Continued)

*Primary Examiner* — Michael J Carey
*Assistant Examiner* — Minqiao Huang
(74) *Attorney, Agent, or Firm* — Xsensus LLP

(57) ABSTRACT

An endoscope includes a camera head including a first sensor having a first number of pixels, the first sensor being configured to receive green (G) light that is light with a G wavelength band, a second sensor having a second number of pixels smaller than the first number of pixels, the second sensor being configured to receive red (R) light that is light with a R wavelength band, and a third sensor having a third number of pixels smaller than the first number of pixels, the third sensor being configured to receive blue (B) light that is light with a B wavelength band.

12 Claims, 10 Drawing Sheets

(51) Int. Cl.
    *A61B 1/05*     (2006.01)
    *A61B 1/06*     (2006.01)

(52) U.S. Cl.
    CPC ............... *A61B 1/045* (2013.01); *A61B 1/05* (2013.01); *A61B 1/0638* (2013.01); *A61B 1/0684* (2013.01)

(56) References Cited

U.S. PATENT DOCUMENTS

| | | | | |
|---|---|---|---|---|
| 2009/0304258 | A1* | 12/2009 | Hayashi | H04N 9/0451 382/144 |
| 2013/0038689 | A1* | 2/2013 | McDowall | H04N 5/232 348/45 |
| 2013/0064436 | A1* | 3/2013 | Tanaka | G06T 7/11 382/128 |
| 2014/0300718 | A1* | 10/2014 | Krattiger | A61B 1/042 348/370 |
| 2015/0094530 | A1* | 4/2015 | Moriya | F21V 5/04 600/103 |
| 2015/0272422 | A1 | 10/2015 | Aoyama | |
| 2015/0313517 | A1* | 11/2015 | Yamaguchi | A61B 1/043 600/335 |
| 2016/0241751 | A1* | 8/2016 | Park | H04N 5/2253 |
| 2016/0270642 | A1* | 9/2016 | Morita | A61B 1/00009 |
| 2016/0270643 | A1* | 9/2016 | Sasaki | A61B 1/051 |
| 2016/0278613 | A1* | 9/2016 | Kuriyama | H04N 9/04555 |

FOREIGN PATENT DOCUMENTS

| | | |
|---|---|---|
| JP | 2014-233533 A | 12/2014 |
| WO | 2016/185733 A1 | 11/2016 |

OTHER PUBLICATIONS

Partial Supplementary European Search Report dated Apr. 9, 2020, issued in corresponding European Patent Application No. 18802646.2, 12 pages.

* cited by examiner

ENDOSCOPE INCLUDING GREEN LIGHT SENSOR WITH LARGER PIXEL NUMBER THAN PIXEL NUMBER OF RED AND BLUE LIGHT SENSORS

CROSS-REFERENCE TO RELATED APPLICATIONS

The present application is based on PCT filing PCT/JP2018/017380, filed May 1, 2018, which claims priority to JP 2017-096200, filed May 15, 2017, the entire contents of each are incorporated herein by reference.

TECHNICAL FIELD

The present technology relates to an endoscope, and particularly to, for example, an endoscope that makes it possible to acquire a high-resolution medical image with low power consumption.

BACKGROUND ART

For example, there has been proposed an endoscope including: an image pickup element for R, an image pickup element for G, and an image pickup element for B that output image signals respectively corresponding to images with red (R) light, green (G) light, and blue (B) light separated from light from an object, in which the image pickup element for R has the number of pixels larger than the respective numbers of pixels of the image pickup element for G and the image pickup element for B, and the image pickup element for R, and the image pickup element for G and the image pickup element for B are disposed such that shifts by a half of pixel of the image pickup element for R are present therebetween to acquire an image with higher resolution to the R light (see, for example, Patent Document 1).

In a case where the image pickup element for R has the number of pixels larger than the respective numbers of pixels of the image pickup element for G and the image pickup element for B, when the image pickup element for R has a light-receiving face (image plane) identical in size to the respective light-receiving faces of the image pickup element for G and the image pickup element for B, the image pickup element for R is smaller in pixel size than the image pickup element for G and the image pickup element for B.

Since small-sized pixels are low in sensitivity, in a case where a scene is captured by the endoscope is a scene that is not dominated by red, an image signal output from the image pickup element for R is an image signal with large noise. Thus, the disposition of the image pickup element for R, and the image pickup element for G and the image pickup element for B each shifted by the half pixel of the image pickup element for R may not function effectively.

CITATION LIST

Patent Document

Patent Document 1: Japanese Patent Laid-Open No. 2008-136732

SUMMARY OF THE INVENTION

Problems to be Solved by the Invention

An image captured by an endoscope is a medical image provided for medical use; thus, it is desirable that an image be a high-resolution image such that a surgeon can verify a detailed part.

Examples of a method of capturing a high-resolution image by an endoscope include a method of using all image sensors with high resolution (multi-pixel image sensors), as an R sensor that receives R light that is light with an R wavelength band, a G sensor that receives G light that is light with a G wavelength band, and a B sensor that receives B light that is light with a B wavelength band.

However, for a high-resolution image sensor, pixel signals (pixel values) of many pixels are transmitted, so that power consumption for processing of transmitting the pixel signals is larger and the amount of heat generation is larger.

The endoscope is operated by a user such as a surgeon or a scopist with the endoscope held by hand. Thus, it is required to reduce the amount of heat generation and hence the power consumption.

The present technology has been made in view of such a situation, and makes it possible to acquire a high-resolution medical image with low power consumption.

Solutions to Problems

A first endoscope of the present technology is an endoscope including: a camera head including: a first sensor having pixels of a first number of pixels, the first sensor being configured to receive green (G) light that is light with a G wavelength band; and a second sensor having pixels of a second number of pixels smaller than the first number of pixels, the second sensor being configured to receive light different from the G light.

According to the first endoscope of the present technology, the first sensor in the camera head has the pixels of the first number of pixels, and receives the green (G) light that is the light in the G wavelength band. The second sensor has the pixels of the second number of pixels smaller than the first number of pixels, and receives the light other than the G light.

A second endoscope according to the present technology is an endoscope including: a camera head including: a first sensor having a predetermined number of pixels of pixels, the first sensor being configured to receive green (G) light that is light with a G wavelength band; and a second sensor having the predetermined number of pixels of pixels, the second sensor being configured to receive light different from the G light, in which the second sensor has a binning function of outputting an added value of pixel values of a plurality of pixels as a pixel value of one pixel, and outputs, with the binning function, a second image having a pixel value corresponding to the light different from the G light, the second image being smaller in the number of pixels than a first image having a pixel value corresponding to the G light, the first image being output from the first sensor.

According to the second endoscope of the present technology, the first sensor has the predetermined number of pixels of pixels, the first sensor being configured to receive the G light that is the light with a green (G) wavelength band, and the second sensor has the predetermined number of pixels of pixels, the second sensor being configured to receive the light different from the G light. The second sensor has the binning function of outputting the added value of the pixel values of the plurality of pixels as the pixel value of the one pixel, and outputs, with the binning function, the second image having the pixel value corresponding to the light different from the G light, the second image being smaller in the number of pixels than the first image having the pixel value corresponding to the G light, the first image being output from the first sensor.

Effects of the Invention

According to the present technology, a high-resolution medical image can be acquired. In particular, according to the present technology, a high-resolution medical image can be acquired with low power consumption.

Note that the effects described herein are not necessarily limited, and any of the effects described in the present disclosure may be applicable.

MODE FOR CARRYING OUT THE INVENTION

<One Embodiment of Endoscopic Surgery System with the Present Technology Applied>

Figure 1:
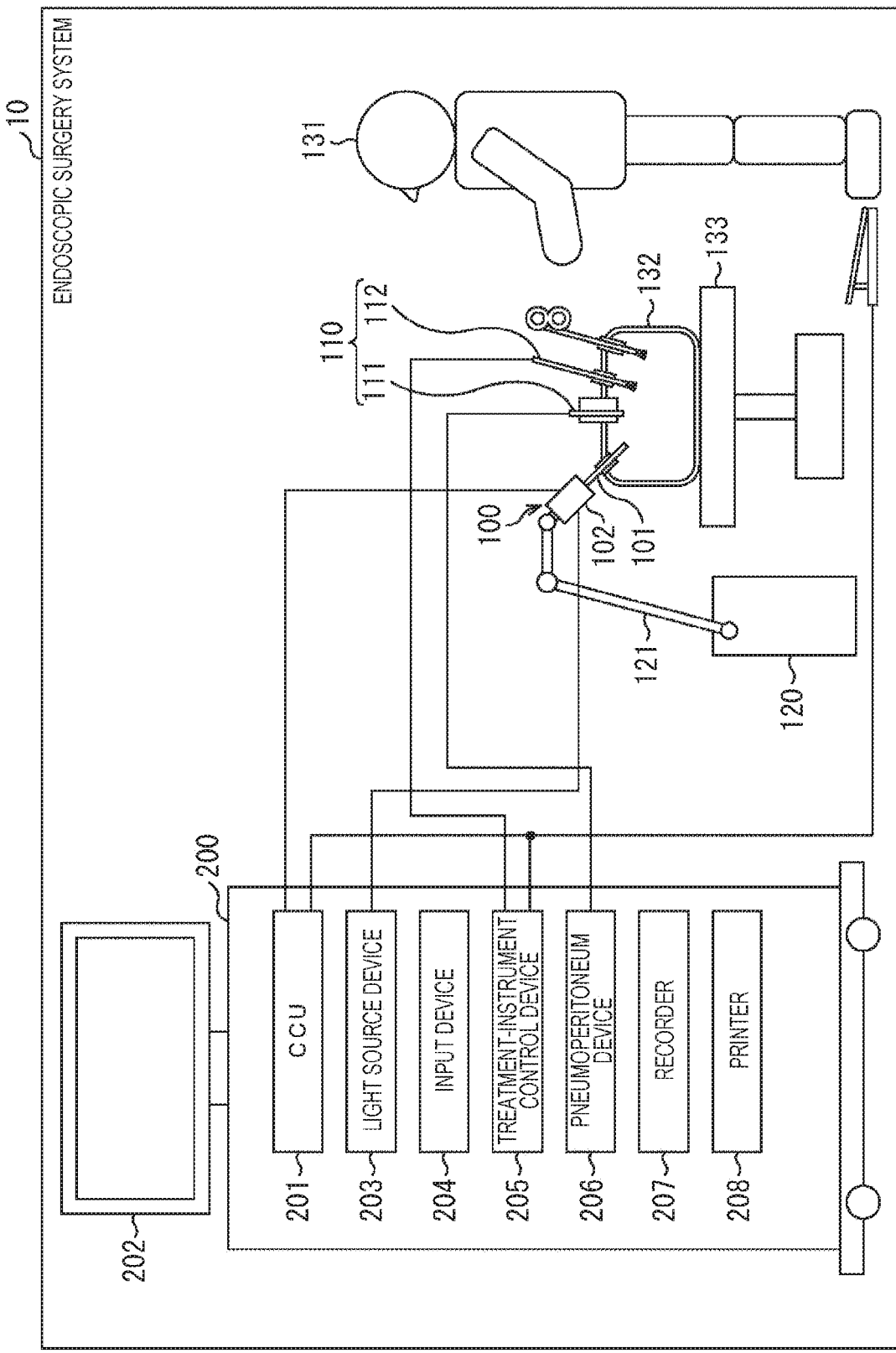
FIG. 1 is an illustration of an exemplary configuration of one embodiment of an endoscopic surgery system with the present technology applied.

FIG. 1 is an illustration of an exemplary configuration of one embodiment of an endoscopic surgery system with the present technology applied.

FIG. 1 illustrates a situation that an operator (surgeon) 131 is performing surgery on a patient 132 on a patient bed 133, with an endoscopic surgery system 10. As illustrated, the endoscopic surgery system 10 includes an endoscope 100; other surgical tools 110 such as a pneumoperitoneum tube 111 and an energy treatment instrument 112; a support arm device 120 for supporting the endoscope 100; and a cart 200 with which various devices for endoscopic surgery are equipped.

The endoscope 100 includes: a lens barrel 101 having a region for insertion into the body cavity of the patient 132, the region having a predetermined length from the distal end; and a camera head 102 connected to the proximal end of the lens barrel 101. In the illustrated example, the endoscope 100 serving as a so-called rigid mirror having the rigid lens barrel 101 is illustrated. The endoscope 100, however, may serve as a so-called flexible mirror having a flexible lens barrel.

An opening with an objective lens fitted thereinto is provided at the distal end of the lens barrel 101. A light source device 203 is connected to the endoscope 100, and light generated by the light source device 203 is guided to the distal end of the lens barrel 101 by a light guide extended inside the lens barrel 101. Thereafter, the guide light is emitted, through the objective lens, to an observation target in the body cavity of the patient 132. Note that the endoscope 100 may be a forward-viewing endoscope, or may be an oblique-viewing endoscope or a side-viewing endoscope.

An optical system and an image sensor (image pickup element) are provided inside the camera head 102, and reflected light (observation light) from the observation target is condensed on the image sensor by the optical system. The image sensor photoelectrically converts the observation light, and generates an electrical signal corresponding to the observation light, that is, an image signal corresponding to an observation image. The image signal is sent, as RAW data, to a camera control unit (CCU) 201.

The CCU 201 includes a central processing unit (CPU), a graphics processing unit (GPU), and the like, and centrally controls the operations of the endoscope 100 and a display device 202. Moreover, the CCU 201 receives the image signal (image data) from the camera head 102, and on the image signal, performs various types of image processing for displaying a medical image corresponding to the image signal, such as development processing (demosaicing).

The display device 202 displays the medical image corresponding to the image signal subjected to the image processing by the CCU 201, in accordance with control from the CCU 201.

The light source device 203 includes, for example, a light source such as a light emitting diode (LED), and supplies, to the endoscope 100, irradiation light for capturing the observation target such as a surgical site.

An input device 204 serves as an input interface to the endoscopic surgery system 10. The user can input various types of information and input instructions to the endoscopic surgery system 10 through the input device 204. For example, the user inputs an instruction such as changing of an image capturing condition (e.g., type of irradiation light, and magnification and focal length) by the endoscope 100.

A treatment-instrument control device 205 controls the driving of the energy treatment instrument 112 for ablation of tissue, incision, sealing of a blood vessel, or the like. The pneumoperitoneum device 206 introduces gas into the body cavity through the pneumoperitoneum tube 111 in order to inflate the body cavity of the patient 132, for the purpose of securing the field of view for the endoscope 100 and securing a working space for the operator. A recorder 207 serves as a device capable of recording various types of information regarding the surgery. A printer 208 serves as a device capable of printing various types of information regarding the surgery in various formats such as text, an image, or a graph.

Note that the light source device 203 that supplies, to the endoscope 100, the irradiation light for capturing of the surgical site can include a white light source including, for example, an LED, a laser light source, or the combination thereof. In a case where the white light source includes a combination of red, green, and blue (RGB) laser light sources, the output intensity and output timing of each color (each wavelength) can be controlled with high precision. Thus, white balance in an image can be adjusted in the light source device 203. Furthermore, in this case, laser light from each of the RGB laser light sources is emitted to the surgical site in time division and the driving of the image sensor of the camera head 102 is controlled in synchronization with the emission timing, so that it is also allowable to capture images, in time division, corresponding to RGB respectively. In a case where the driving of the image sensor is controlled as described above, a color image can be obtained without providing a color filter to the image sensor.

Furthermore, the driving of the light source device 203 may be controlled so as to change the intensity of light to be output at predetermined time intervals. The driving of the image sensor of the camera head 102 is controlled in synchronization with the timing of the change of the light intensity, images in time division are acquired and combined. As a result, a high-dynamic range image that does not have so-called blown-out highlights and blocked-up shadows can be generated.

Furthermore, the light source device 203 may be able to supply light with a predetermined wavelength band corresponding to special light observation. In special light observation, for example, so-called narrow-band light observation (narrow band imaging) is performed in which with the wavelength dependency on light absorption in body tissue, light narrower in band than irradiation light (i.e., white light) at normal observation is emitted to capture, with high contrast, predetermined tissue such as a blood vessel of a mucous membrane surface layer. Alternatively, in special light observation, fluorescence observation may be performed in which an image is obtained with fluorescence generated by emission of excitation light. Fluorescence observation enables observation of fluorescence from body tissue by emission of excitation light to the body tissue (autofluorescence observation), or obtaining of a fluorescence image by local injection of a reagent such as indocyanine green (ICG) through body tissue and emission of excitation light corresponding to the fluorescence wavelength of the reagent, to the body tissue, for example. The light source device 203 can supply narrow band light and/or excitation light corresponding to such special light observation.

<First Exemplary Configuration of Camera Head 102 and First Exemplary Configuration of CCU 201>

Figure 2:
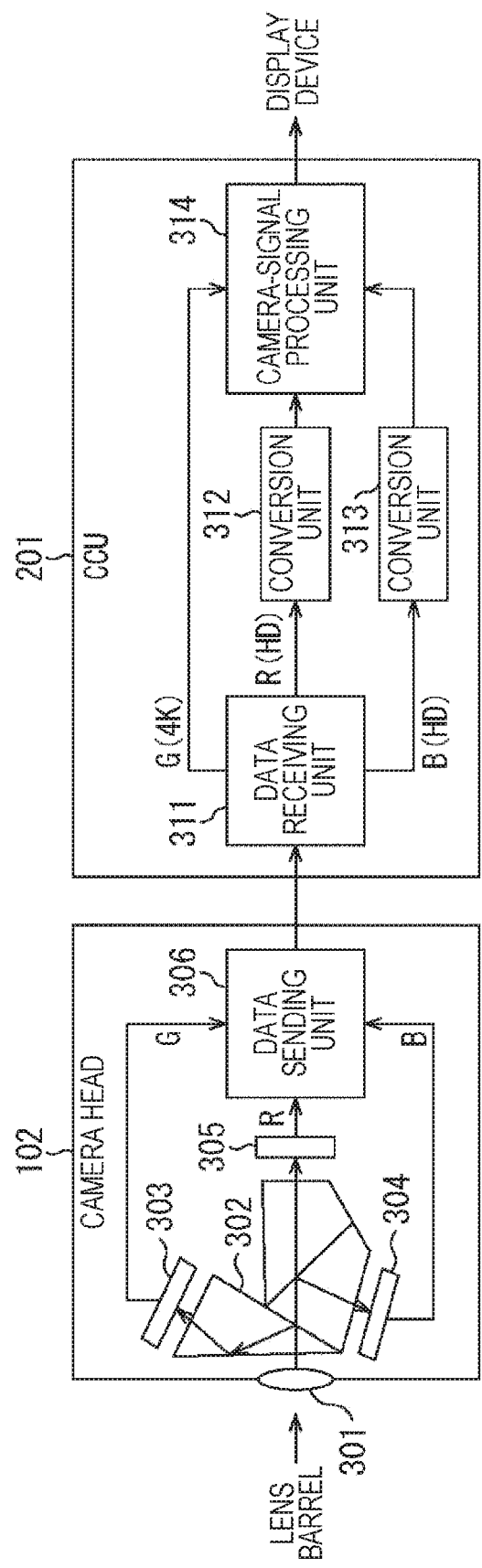
FIG. 2 is a block diagram of a first exemplary configuration of a camera head 102 and a first exemplary configuration of a camera control unit (CCU) 201.

FIG. 2 is a block diagram of a first exemplary configuration of the camera head 102 and a first exemplary configuration of the CCU 201.

Note that, in order to simplify the description, FIG. 2 (similarly to even in figures as described later) omits an illustration of a configuration in which irradiation light is emitted to a surgical site.

In FIG. 2, the camera head 102 is a monocular camera head, and includes: a lens (group) 301; a prism 302; image sensors 303, 304, and 305; and a data sending unit 306.

Here, the camera head 102 may include multiple eyes, instead of a single eye. However, in a case where the camera head 102 includes a single eye, the camera head 102 can be made smaller, so that the burden on the user holding the camera head 102 can be reduced.

Furthermore, a part included in the camera head 102, that is, for example, the lens 301, the prism 302, or the image sensors 303 to 305 can be provided at the distal end of the lens barrel 101.

The lens 301 is included in the optical system of the camera head 102 and causes light entered from the lens barrel 101, that is, reflected light that returns after the irradiation light is reflected on the surgical site, to condense on the image sensors 303 to 305 through the prism 302.

The prism 302 is included in the optical system of the camera head 102. The light condensed by the lens 301 enters the prism 302. The prism 302 separates the light from the lens 301 into R light, G light, and B light, and causes the G light to enter the image sensor 303, the B light to enter the image sensor 304, and the R light to enter the image sensor 305, respectively.

The image sensor 303 receives the G light entered from the prism 302, and performs photoelectric conversion to output a G signal as an image signal corresponding to the G light from the prism 302.

The image sensor 304 receives the B light entered from the prism 302, and performs photoelectric conversion to output a B signal as an image signal corresponding to the B light from the prism 302.

The image sensor 305 receives the R light entered from the prism 302, and performs photoelectric conversion to output an R signal as an image signal corresponding to the R light from the prism 302.

The G signal output from the image sensor 303, the B signal output from the image sensor 304, and the R signal output from the image sensor 305 are supplied to the data sending unit 306.

Here, the image sensors 303 to 305 are image sensors having respective light-receiving faces identical in size, each light-receiving face being capable of receiving light to perform photoelectric conversion. The image sensors 303 to 305 are disposed such that images of the same object are formed identically in size on the light-receiving faces.

Furthermore, the number of pixels (second number of pixels) of each of the image sensors 304 and 305 (second sensors) that receive light different from the G light is smaller than the number of pixels (first number of pixels) of the image sensor 303 (first sensor) that receives the G light.

Thus, assuming that the image sensor 303 is a high-resolution image sensor capable of capturing a so-called 4K image with, for example, 3840×2160 pixels or 4096×2160 pixels in lateral×longitudinal, the image sensors 304 and 305 are image sensors lower in resolution than the image sensor 303, the image sensors 304 and 305 being capable of capturing a so-called high definition (HD) image with, for example, 1920×1080 pixels.

As described above, according to the present embodiment, the respective light-receiving faces of the image sensors 303 to 305 are identical in size; however, the image sensors 304 and 305 are smaller in the number of pixels than the image sensor 303. Thus, the image sensors 304 and 305 are larger (can be larger) in pixel size (pitch) than the image sensor 303.

Therefore, the image sensor 303 that receives the G light is an image sensor larger in the number of pixels (despite high resolution) but smaller in pixel size than the image sensors 304 and 305.

Furthermore, the image sensors 304 and 305 that receive light different from the G light, that is, here the B light and the R light respectively, are image sensors larger in pixel size but smaller in the number of pixels (lower in resolution) than the image sensor 303.

The data sending unit 306 transmits (sends), to the CCU 201, the G signal, the B signal, and the R signal respectively supplied from the image sensors 303 to 305.

At the camera head 102 having the configuration as described above, the light entered from the lens barrel 101 enters the prism 302 through the lens 301. At the prism 302, the light from the lens 301 is separated into the R light, the G light, and the B light, and the prism 302 causes the G light to enter the image sensor 303, the B light enter to the image sensor 304, and the R light to enter the image sensor 305, respectively.

The image sensors 303 to 305 respectively receive the G light, the B light, and the R light from the prism 302, and output a corresponding G signal, B signal, and R signal, to the data sending unit 306.

The data sending unit 306 sends, to the CCU 201, the G signal, the B signal, and the R signal from the respective image sensors 303 to 305.

For the camera head 102, the high-resolution image sensor, that is, the image sensor capable of capturing, for example, a 4K image (hereinafter, also referred to as 4K sensor) is adopted as the image sensor 303 that receives the G light, and the image sensors each smaller in the number of pixels than the 4K sensor, that is, for example, the image sensors capable of capturing an HD image (hereinafter, also referred to as HD sensor) are adopted as the image sensors 304 and 305 that respectively receive the B light and the R light different from the G light. Thus, a high-resolution medical image (medical image viewable in high resolution) can be acquired with low power consumption.

In other words, human vision has a characteristic of being more sensitive to G light (G signal) than, for example, R light and B light different from the G light, and obtaining resolution information from the G light.

Thus, the G light contributes to resolution that human vision obtains (senses) more than the R light and the B light.

For the camera head 102, the image sensor 303 that receives the G light contributing to the resolution as described above is the high-resolution image sensor (e.g., 4K sensor) larger in the number of pixels than each of the image sensor 304 that receives the B light and the image sensor 305 that receives R light. Thus, use of the G signal output from such an image sensor 303 enables acquisition of a high-resolution medical image.

In other words, (an image signal of) a medical image finally displayed on the display device 202 is generated from the G signal output from the image sensor 303, the B signal output from the image sensor 304, and the R signal output from the image sensor 305.

The image sensors 304 and 305 are, for example, the HD sensors, each smaller in the number of pixels than the image sensor 303, that is, for example, the 4K sensor. In addition, the B signal and the R signal respectively output from the image sensors 304 and 305 are lower in degree of contribution to the resolution (sensed by human) (hereinafter, also referred to as degree of resolution contribution) than the G signal output from the image sensor 303.

In contrast, the image sensor 303 that outputs the G signal higher in degree of resolution contribution is the high-resolution 4K sensor. Thus, a medical image generated from the G signal output from the image sensor 303, the B signal output from the image sensor 304, and the R signal output from the image sensor 305 is an image having a resolution that can be sensed almost similar to a case where high-resolution 4K sensors are all used as the image sensors 303 to 305.

Furthermore, the image sensors 304 and 305 are, for example, HD sensors, the image sensors 304 and 305 respectively receiving the B light and the R light that do not contribute to the resolution as much as the G light and being smaller in the number of pixels than the image sensor 303 that receives the G light that contributes to the resolution. Thus, power consumption required for sending the B signal and the R signal respectively output from the image sensors 304 and 305 is lower in comparison to a case where, for example, 4K sensors, which are identical in resolution to the high-resolution image sensor 303, are used as the image sensors that respectively receive the B light and the R light. As a result, the amount of heat generation can be reduced.

For example, as each of the image sensors 304 and 305, in a case where an image sensor having N/4 number of pixels that is a quarter of the number of pixels N of the image sensor 303 is adopted (e.g., the number of lateral pixels and the number of longitudinal pixels each are a half of the number of pixels of the image sensor 303), the sum of the respective numbers of pixels of the image sensors 303 to 305 satisfies 3N/2=N+N/4+N/4. In a case where image sensors identical in the number of pixels to the image sensor 303 are adopted as the image sensors 304 and 305, the sum of the respective numbers of pixels of the image sensors 303 to 305 satisfies a half of (3N=N+N+N).

Now, in order to simplify the description, it is assumed that power consumption required for sending the pixel signals (G signal, B signal, and R signal) respectively output from the image sensors 303 to 305 is proportional to the respective numbers of pixels of the image sensors 303 to 305. Then, in a case where image sensors each having the number of pixels of a quarter of the number of pixels of the image sensor 303 are adopted as the image sensors 304 and 305, the power consumption and hence the amount of heat generation can be reduced by a half of a case where image sensors identical in the number of pixels to the image sensor 303 are adopted as the image sensors 304 and 305.

Furthermore, in the camera head 102, the image sensors 304 and 305 that respectively receive the B light and the R light different from the G light are smaller in the number of pixels (lower in resolution) but larger in pixel size than the image sensor 303. In other words, the image sensors 304 and 305 are image sensors higher in sensitivity to the light intensity than the image sensor 303 and can obtain the pixel signals (B signal and R signal) with lower noise (better in signal to noise ratio (S/N)).

The medical image finally displayed on the display device 202 is generated by using such a B signal and R signal with lower noise, so that a medical image having a better S/N can be obtained.

Furthermore, an image sensor with a small number of pixels is less expensive than an image sensor with a large number of pixels. Thus, the adoption of the image sensors smaller in the number of pixels than image sensor 303, as the image sensors 304 and 305, allows the camera head 102 and hence the endoscopic surgery system 10 to have a configuration less expensive in comparison to a case where the image sensors identical in the number of pixels to the image sensor 303 are adopted as the image sensors 304 and 305.

Note that the image sensor 303 is not limited to the 4K sensor, and, for example, an 8K sensor that is an image sensor capable of capturing an 8K image with much higher resolution can be adopted. Similarly, the image sensors 304 and 305 are not limited to the HD sensors.

Moreover, the combination of the image sensor 303 with the image sensors 304 and 305 is not limited to the combination of the 4K sensor and the HD sensors. For example, as a combination of the image sensor 303 with the image sensors 304 and 305, a combination of an 8K sensor and a 4K sensor, or the like can be adopted.

Furthermore, the respective light-receiving faces of the image sensors 303 to 305 may not be identical in size. Moreover, the pixel size of the image sensor 303 is not limited to the pixel size smaller than the pixel size of each of the image sensors 304 and 305.

For example, there can be adopted a pixel size identical between the image sensor 303 and the image sensors 304 and 305. In this case, the light-receiving face of the image sensor 303 larger in the number of pixels is larger in size than the respective light-receiving faces of the image sensors 304 and 305 smaller in the number of pixels.

Moreover, for the endoscope described in Patent Document 1 described above, the image pickup element for R, and the image pickup element for G and the image pickup element for B are disposed such that shifts by a half of pixel are present therebetween. Thus, the number of lateral pixels and the number of longitudinal pixels of the image pickup element for R needs to be an integral multiple of the number of lateral pixels and the number of longitudinal pixels of each of the image pickup element for G and the image pickup element for B. In contrast, for the camera head 102, the number of pixels of the image sensor 303 may or may not be an integral multiple of the respective numbers of pixels of the image sensors 304 and 305. In other words, restriction on the integral multiple is not imposed on the relationship between the number of pixels of the image sensor 303 and the respective numbers of pixels of the image sensors 304 and 305.

In FIG. 2, the CCU 201 includes a data receiving unit 311, conversion units 312 and 313, and a camera-signal processing unit 314.

The data receiving unit 311 receives the G signal, the B signal, and the R signal sent from the data sending unit 306, and supplies the received signals to necessary blocks.

In FIG. 2, the G signal is supplied to the camera-signal processing unit 314, the R signal to the conversion unit 312, and the B signal to the conversion unit 313, respectively.

The conversion unit 312 performs image processing of converting (upconverting) the number of pixels of (the image signal of) an R image having the R signal from the data receiving unit 311 as a pixel value, into the number of pixels identical to the number of pixels of a G image having the G signal output from the image sensor 303 as a pixel value, and supplies the R image after the conversion to the camera-signal processing unit 314.

The conversion unit 313 performs image processing of converting the number of pixels of a B image having the B signal from the data receiving unit 311 as a pixel value, into the number of pixels identical to the number of pixels of the G image, and supplies the B image after the conversion to the camera-signal processing unit 314.

The conversion (upconversion) of the number of pixels at the conversion units 312 and 313 can be performed with, for example, a filter for upconversion, such as a bicubic filter. The conversion of the number of pixels at the conversion units 312 and 313 can be performed regardless of whether or not the number of pixels of the image sensor 303 is an integral multiple of the respective numbers of pixels of the image sensors 304 and 305. Therefore, as described above, the number of pixels of the image sensor 303 may or may not be an integral multiple of the respective numbers of pixels of the image sensors 304 and 305.

The camera-signal processing unit 314 performs predetermined camera-signal processing on the G image having the G signal from the data receiving unit 311 as the pixel value, the R image from the conversion unit 312 converted into the number of pixels identical to the number of pixels of the G image, and the B image from the conversion unit 313 converted into the number of pixels identical to the number of pixels of the G image, and the camera-signal processing unit 314 generates a medical image having the R signal, the G signal, and the B signal as respective pixel values to supply the medical image to the display device 202.

As the camera-signal processing, for example, various types of signal processing such as development, gamma correction, and color adjustment can be performed.

<Respective Exemplary Configurations of Image Sensors 303 to 305>

Figure 3:
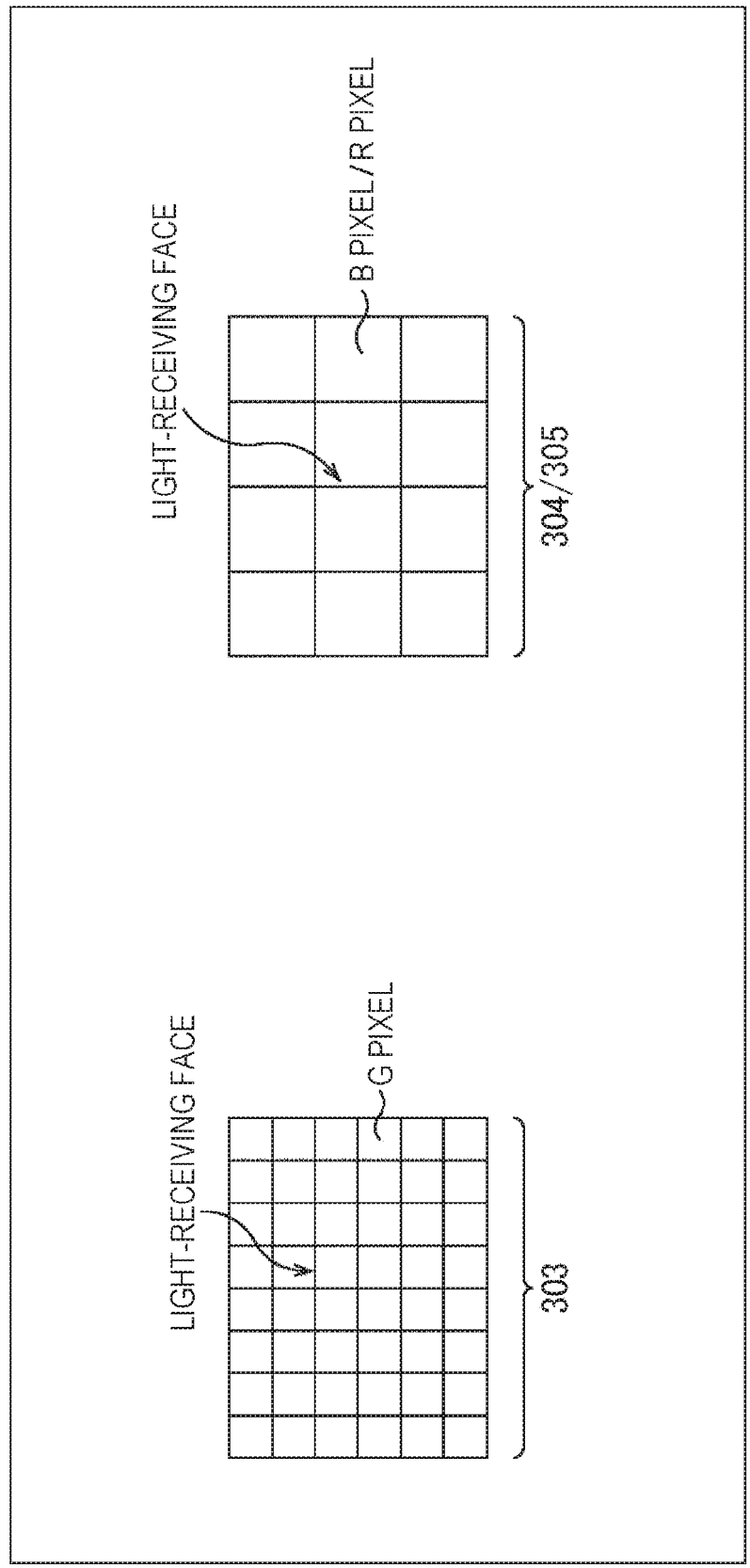
FIG. 3 is an explanatory plan view of the overview of respective exemplary configurations of image sensors 303 to 305.

FIG. 3 is an explanatory plan view of the overview of the respective exemplary configurations of the image sensors 303 to 305.

In other words, FIG. 3 schematically illustrates the respective exemplary configurations of the image sensors 303 to 305.

In FIG. 3, the respective light-receiving faces of the image sensors 303 to 305 are identical in size.

However, the image sensors 304 and 305 are smaller in the number of pixels than the image sensor 303.

Thus, as described in FIG. 2, the image sensor 303 that receives G light is smaller in pixel size but larger in the number of pixels than the image sensors 304 and 305, and the image sensor 303 can capture a high-resolution image.

Furthermore, the image sensors 304 and 305 that respectively receive the B light and the R light are smaller in the number of pixels but larger in pixel size than the image sensor 303, and the image sensors 304 and 305 are higher in sensitivity to the light intensity than the image sensor 303.

<Processing by CCU 201>

Figure 4:
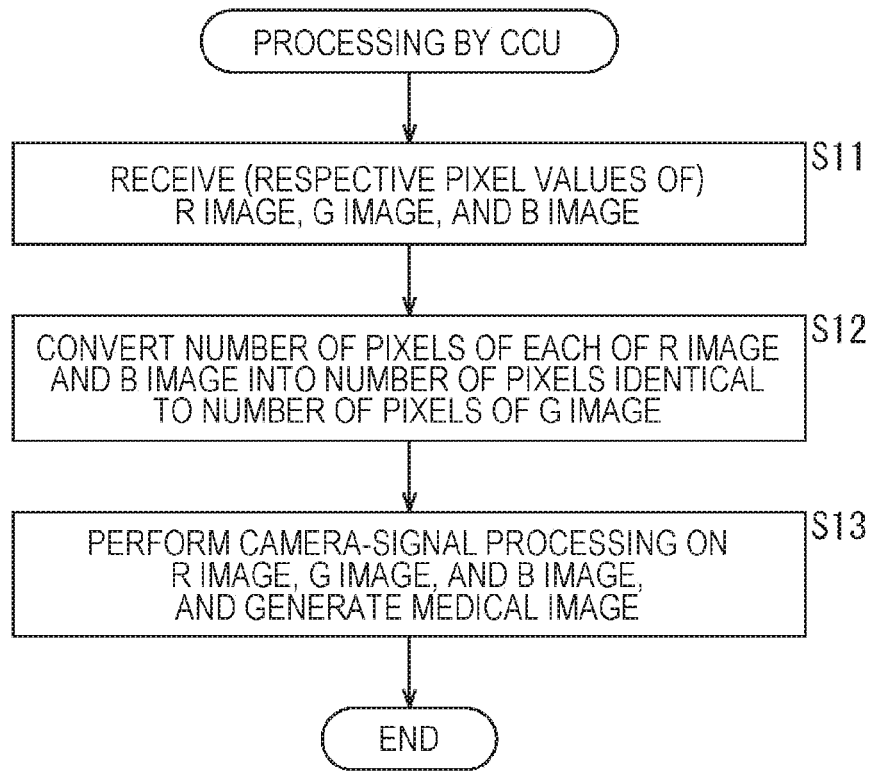
FIG. 4 is a flowchart for describing exemplary processing by the CCU 201.

FIG. 4 is a flowchart for describing exemplary processing by the CCU 201 of FIG. 2.

In step S11, the data receiving unit 311 receives the G image having the G signal as a pixel value, the B image having the B signal as a pixel value, and the R image having the R signal as a pixel value each sent from the data sending unit 306. Moreover, in step S11, the data receiving unit 311 respectively supplies the G image to the camera-signal processing unit 314, the R image to the conversion unit 312, and the B image to the conversion unit 313, and then the processing proceeds to step S12.

In step S12, the conversion unit 312 converts the number of pixels of the R image from the data receiving unit 311, into the number of pixels identical to the number of pixels of the G image, and the conversion unit 313 converts the number of pixels of the B image from the data receiving unit 311, into the number of pixels identical to the number of pixels of the G image. Moreover, in step S12, the conversion unit 312 supplies the R image after the conversion of the number of pixels, to the camera-signal processing unit 314, and the conversion unit 313 supplies the B image after the conversion of the number of pixels, to the camera-signal processing unit 314, and then the processing proceeds to step S13.

In step S13, the camera-signal processing unit 314 performs predetermined camera-signal processing on the G image having the G signal from the data receiving unit 311 as the pixel value, the R image from the conversion unit 312, and the B image from the conversion unit 313, and the camera-signal processing unit 314 generates a medical image having the R signal, the G signal, and the B signal as respective pixel values to supply the medical image to display device 202, and then the processing ends.

<Second Exemplary Configuration of CCU 201>

Figure 5:
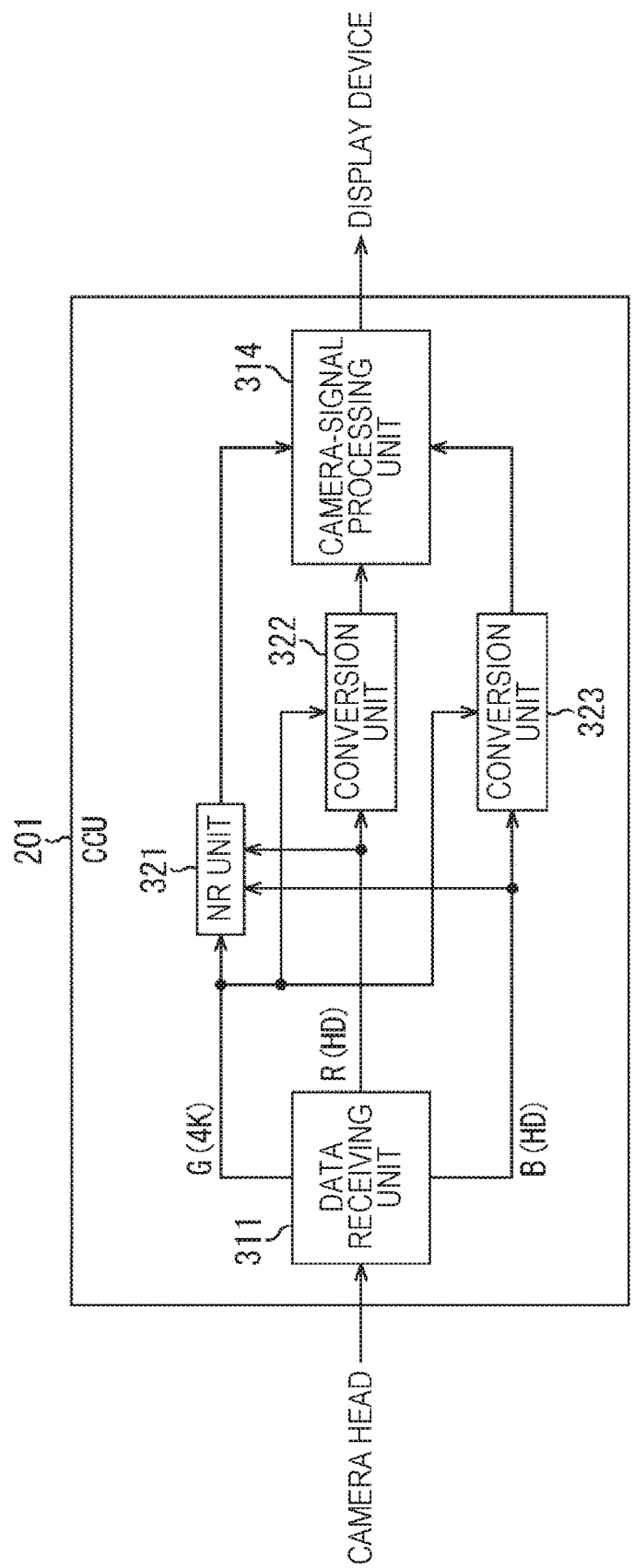
FIG. 5 is a block diagram of a second exemplary configuration of the CCU 201.

FIG. 5 is a block diagram of a second exemplary configuration of the CCU 201.

Note that in the figure, the same reference signs are given to parts corresponding to the case of FIG. 2, and the description of the corresponding parts will be appropriately omitted below.

In FIG. 5, a CCU 201 includes a data receiving unit 311, a camera-signal processing unit 314, a noise reduction (NR) unit 321, and conversion units 322 and 323.

Thus, the CCU 201 of FIG. 5 is common to the case of FIG. 2 in that the data receiving unit 311 and the camera-signal processing unit 314 are included. The CCU 201 of FIG. 5, however, is different from the case of FIG. 2 in that the NR unit 321 is newly provided and in that conversion units 322 and 323 are provided instead of the conversion units 312 and 313.

A G image, an R image, and a B image are supplied to the NR unit 321 from the data receiving unit 311.

The NR unit 321 performs, for example, NR as image processing on the G image (first image), with the R image and the B image (second images). The NR can be performed as filtering with a Bilateral filter, for example.

Here, the NR unit 321 can perform, with the R image and the B image, NR on a part of the G image, the part being a threshold or greater in correlation with the R image and the B image (region having a higher correlation), and can perform, without using the R image and the B image, NR on a part of the G image, the part not being the threshold or greater in correlation with the R image and the B image.

In other words, the B image and the R image are images with lower noise, obtained by the image sensors 304 and 305 higher in sensitivity to the light intensity. Thus, regarding part of the G image, having a higher correlation in terms of the waveform pattern of a pixel value at the same phase (the same position) as the R image and the B image, NR such as filtering with a JointBilateral filter is performed with the R image and the G image each having a higher correlation with the G image, in addition to the G image. As a result, noise of the G image can be further reduced with the R image and the B image with lower noise.

In contrast, regarding part of the G image, having a lower correlation in terms of the waveform pattern of the pixel value at the same phase as the R image and the B image, NR such as filtering with a Bilateral filter can be performed with the G image, without using the R image and the B image.

The G image and the R image are supplied to the conversion unit 322 from the data receiving unit 311.

As image processing on the R image (second image) from the data receiving unit 311, the conversion unit 322 performs, for example, upconversion in which, with the G image (first image), the number of pixels of the R image is converted into the number of pixels identical to the number of pixels of the G image.

Here, the conversion unit 322 can perform upconversion with the G image for part of the R image, the part being a threshold or greater in correlation with the G image, and can perform upconversion without using the G image for part of the R image, the part being not the threshold or greater in correlation with the G image.

In other words, the G image is the high-resolution image obtained by the image sensor 303 larger in the number of pixels. Thus, regarding part of the R image, having a higher correlation in terms of the waveform pattern of a pixel value at the same phase as the G image, for example, upconversion by filtering such as JointBilateralUpsampling is performed with the G image having a higher correlation with the R image. As a result, the R image having a higher resolution can be obtained, in comparison to a case where upconversion is performed without using the G image.

In contrast, regarding part of the R image, having a lower correlation in terms of the waveform pattern of the pixel value at the same phase as the G image, for example, upconversion by filtering with a bicubic filter can be performed similarly to the conversion unit 312 of FIG. 2, without using the G image.

The G image and the B image are supplied from the data receiving unit 311 to the conversion unit 323.

The conversion unit 323 performs processing similarly to the conversion unit 322 except that the B image is used instead of the R image, and thus the description thereof is omitted.

Here, in the NR unit 321, in order to perform the NR on the G image with use of the R image and the B image, it is sufficient if the positional relationship between the G image and each of the R image and the B image (positions where the same object is imaged in the G image and each of the R image and the B image) can be recognized. Restriction, for example, the number of pixels of the G image must be an integral multiple of the respective numbers of pixels of the R image and the B image, is not particularly imposed on the relationship between the number of pixels of the image sensor 303 and the respective numbers of pixels of the image sensors 304 and 305.

For the above points, the same is applied to a case where the upconversion with the G image is performed on the R image in the conversion unit 322, and a case where the upconversion with the G image is performed on the B image in the conversion unit 323.

<Second Exemplary Configuration of Camera Head 102>

Figure 6:
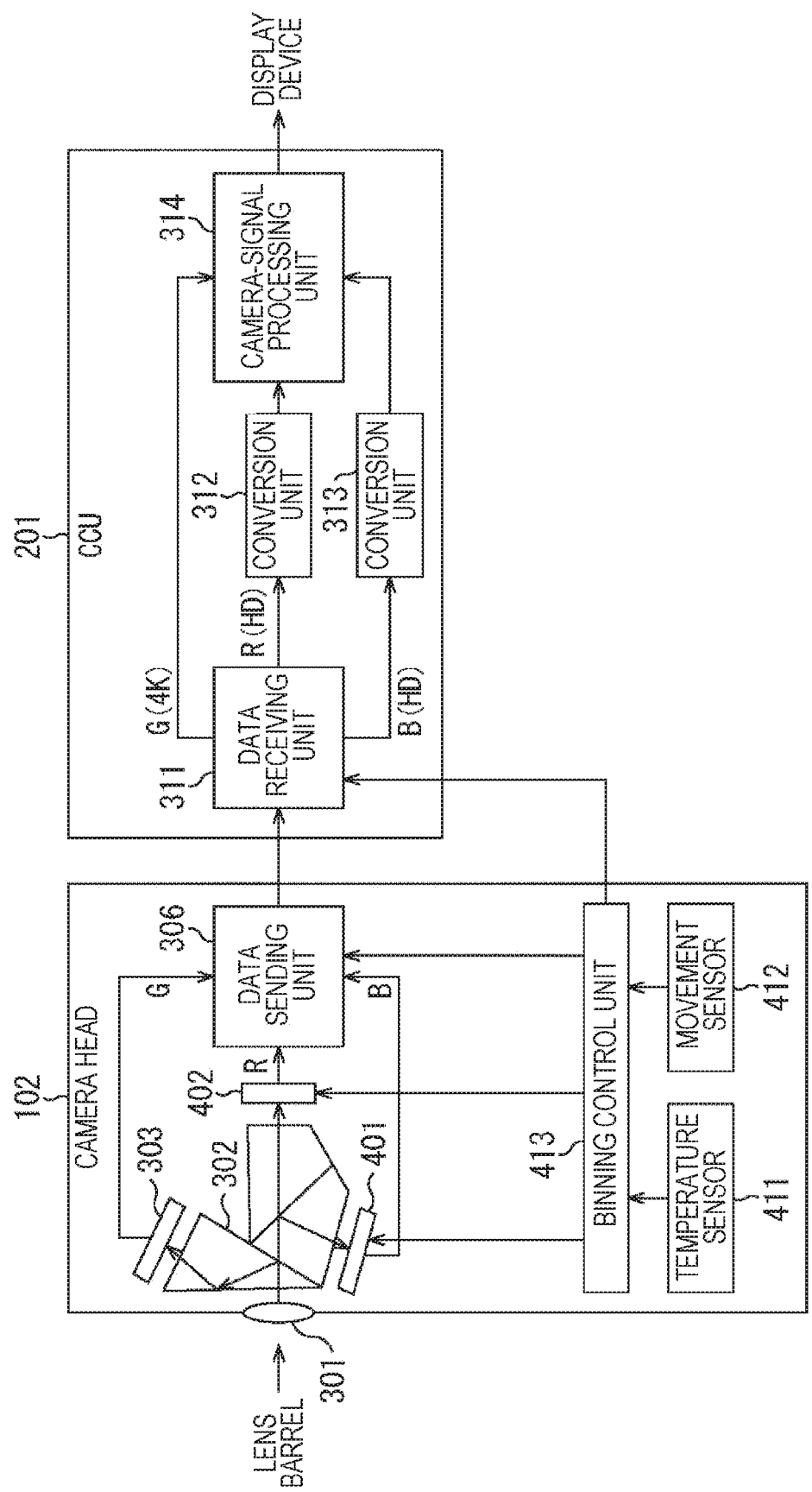
FIG. 6 is a diagram of a second exemplary configuration of the camera head 102.

FIG. 6 is a diagram of a second exemplary configuration of the camera head 102.

Note that in the figure, the same reference signs are given to parts corresponding to the case of FIG. 2, and the description of the corresponding parts will be appropriately omitted below.

Furthermore, in FIG. 6, the first exemplary configuration of the CCU 201 of FIG. 2 is adopted as the configuration of the CCU 201. The second exemplary configuration of the CCU 201, however, can be adopted as the configuration of the CCU 201 of FIG. 5.

In FIG. 6, a camera head 102 includes a lens 301, a prism 302, an image sensor 303, a data sending unit 306, image sensors 401 and 402, a temperature sensor 411, a movement sensor 412, and a binning control unit 413.

Thus, the camera head 102 of FIG. 6 is common to the case of FIG. 2 in that the lens 301, the prism 302, the image sensor 303, and the data sending unit 306 are included. The camera head 102 of FIG. 6, however, is different from the case of FIG. 2 in that the image sensors 401 and 402 are provided instead of the image sensors 304 and 305, and in that the temperature sensor 411, the movement sensor 412, and the binning control unit 413 are newly provided.

Similarly to the image sensors 304 and 305 of FIG. 2, the image sensors 401 and 402 respectively receive B light and R light entered from the prism 302 and perform photoelectric conversion to output (respective image signals of) a B image and an R image corresponding to the B light and the R light from the prism 302, to the data sending unit 306.

Here, similar to the image sensors 304 and 305 of FIG. 2, the image sensors 401 and 402 are image sensors having respective light-receiving faces identical in size to the image sensor 303, and are disposed similarly to the image sensors 304 and 305.

However, the image sensors 401 and 402 (second sensors) each have the number of pixels (predetermined number of pixels) identical to the number of pixels of the image sensor 303 (first sensor). Thus, the image sensors 401 and 402 are, for example, 4K sensors, similar to the image sensor 303.

Moreover, in addition to a function of outputting the added value of the pixel values of one pixel as a pixel value of one pixel, the image sensors 401 and 402 each have a binning function of outputting the added value of the pixel values of a plurality of pixels, for example, a 2×2 pixel in lateral×longitudinal, as a pixel value of one pixel.

Now, for the image sensors 401 and 402, an operation mode that enables the function of outputting the added value of the pixel values of one pixel as the pixel value of one pixel is referred to as a normal mode, and an operation mode that enables the binning function is referred to as a binning mode.

In the normal mode, the image sensors 401 and 402 respectively output a B image and an R image (second images) each having the number of pixels identical to the number of pixels of the G image (first image) output from the image sensor 303.

In contrast, in the binning mode, the image sensors 401 and 402 respectively output, with the binning function, a B image and an R image (second images) having pixel values respectively corresponding to B light and R light, the B image and the R image being smaller in the number of pixels than a G image (first image) output from the image sensor 303, the G image having a pixel value corresponding to G light.

In other words, in the normal mode, the image sensors 401 and 402 respectively output, for example, 4K images identical in the number of pixels to the G image, as the B image and the R image. In contrast, in the binning mode, the image sensors 401 and 402 respectively output, for example, HD images smaller in the number of pixels than the G image, as the B image and the R image.

As described above, in the normal mode, the image sensors 401 and 402 respectively output, as the B image and the R image, the high-resolution 4K images similar to the G image. Thus, power consumption required for sending the B image and the R image and hence the amount of heat generation increase. However, the B image and the R image are the high-resolution images similar to the G image, so that a medical image generated with such a B image and an R image is a high-resolution image.

In contrast, in the binning mode, the image sensors 401 and 402 respectively output, as the B image and the R image, the HD images smaller in the number of pixels than the G image. Thus, a medical image generated with the B image and the R image is lower in resolution, in comparison to the case of the normal mode. However, the B image and the R image in the binning mode are the images (HD images) smaller in the number of pixels, in comparison to the case of the normal mode (4K images). Thus, power consumption required for sending the B image and the R image and hence the amount of heat generation decrease, and the image sensors 401 and 402 each increase in the sensitivity to the light intensity, so that the respective S/N ratios of the B image and the R image improves.

The temperature sensor 411 senses the temperature of the camera head 102, and supplies temperature information indicating the temperature to the binning control unit 413.

The movement sensor 412 includes, for example, a gyro, senses the movement of the camera head 102, and then supplies movement information indicating the movement, to the binning control unit 413.

The binning control unit 413 recognizes a state of the camera head 102 on the basis of, for example, the temperature information from the temperature sensor 411 and the movement information from the movement sensor 412, and controls the respective operation modes of the image sensors 401 and 402, in accordance with the state of the camera head 102.

For example, in a case where on the basis of the temperature information, the state of the camera head 102 is recognized as high in temperature, the binning control unit 413 can set the respective operation modes of the image sensors 401 and 402 to the binning mode. In this case, the power consumption of the camera head 102 and hence the amount of heat generation can be lowered.

In contrast, in a case where it is recognized that the state of the camera head 102 is low in temperature, the binning control unit 413 can set the respective operation modes of the image sensors 401 and 402 to the normal mode. In this case, a high-resolution medical image can be acquired.

Furthermore, for example, in a case where on the basis of the movement information, it is recognized that the camera head 102 is moving slowly (including stationary), the binning control unit 413 can set the respective operation modes of the image sensors 401 and 402 to the normal mode. As a result, a high-resolution medical image can be acquired. In a case where the camera head 102 is stationary, it is estimated that the user is gazing at the part imaged in a medical image. Thus, acquisition of a high-resolution medical image allows the user to accurately verify the details of a desired site while the high-resolution medical image is viewed.

In contrast, in a case where it is recognized that the camera head 102 is moving fast, the binning control unit 413 can set the respective operation modes of the image sensors 401 and 402 to the binning mode. As a result, the power consumption and the amount of heat generation of the camera head 102 can be lowered. In a case where the camera head 102 is moving at some velocity, it is estimated that a site to be captured is searched with the camera head 102 moved. Thus, a medical image may not have a resolution as high as a resolution in a case where the camera head 102 is stationary, so that priority can be given to the lowering of the power consumption and the amount of heat generation.

Here, the data amount of an image transmitted (sent) from the data sending unit 306 to the data receiving unit 311 is different between the normal mode and the binning mode. Thus, the binning control unit 413 controls the data sending unit 306 and the data receiving unit 311, in accordance with the respective operation modes of the image sensors 401 and 402. As a result, the binning control unit 413 controls, for example, the transmission rate between the data sending unit 306 and the data receiving unit 311, and a period of time for transmitting an image.

Note that in the FIG. 6, the temperature sensor 411 and the movement sensor 412 each are provided as a sensor that detects the state of the camera head 102. However, as the sensor that detects the state of the camera head 102, either only the temperature sensor 411 or the movement sensor 412 can be provided, or a sensor that detects a different state can be provided.

Furthermore, the binning control unit 413 can set the respective operation modes of the image sensors 401 and 402, in accordance with a state different from the temperature or the movement of the camera head 102.

Moreover, the binning control unit 413 can set the respective operation modes of the image sensors 401 and 402, in response to an operation by the user. For example, the user can select the normal mode in a case where the user desires to verify a minute part imaged in a medical image, and can select the binning mode in a case where the user desires to view a medical image with a better S/N.

Furthermore, in FIG. 6, in a case where the respective operation modes of the image sensors 401 and 402 are in the binning mode, the conversion unit 312 of the CCU 201 upconverts the R image supplied from the data receiving unit 311, and in a case where the respective operation modes are in the normal mode, the conversion unit 312 of the CCU 201 supplies, to the camera-signal processing unit 314, the R image supplied from the data receiving unit 311 as it is without performing upconversion. This is because, in the normal mode, the R image is a 4K image identical in the number of pixels to the G image and does not need to be upconverted. The conversion unit 313 also performs in a similar manner.

Figure 7:
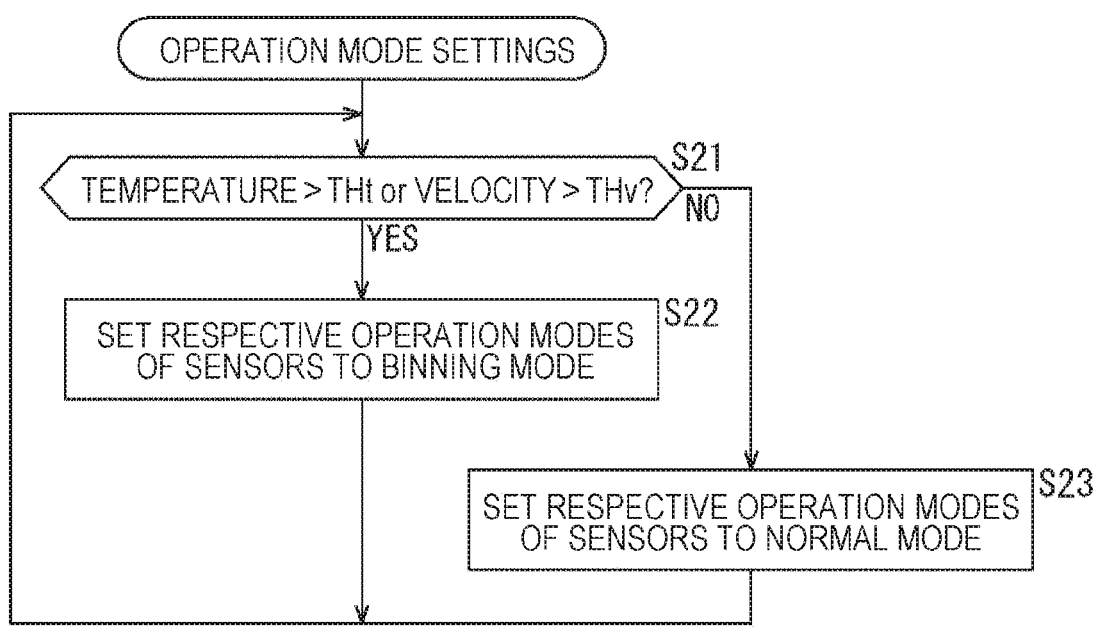
FIG. 7 is a flowchart for describing exemplary processing of operation mode settings performed by a binning control unit 413.

FIG. 7 is a flowchart for describing exemplary processing of the operation mode settings performed by the binning control unit 413 of FIG. 6.

In step S21, on the basis of the temperature information from the temperature sensor 411 and the movement information from the movement sensor 412, the binning control unit 413 determines whether the temperature of the camera head 102 is greater than a temperature threshold THt, or whether the velocity of the movement of the camera head 102 is greater than a velocity threshold THv.

In a case there it is determined in step S21 that the temperature of the camera head 102 is greater than the threshold THt, or in a case where it is determined that the velocity of movement of the camera head 102 is greater than the threshold THv, the processing proceeds to step S22.

In step S22, the binning control unit 413 sets the respective operation modes of the image sensors 401 and 402 to the binning mode, and the processing returns to step S21. In this case, similarly to the case of FIG. 2, the resolution of a medical image can be increased to some extent (medical image viewable in high resolution can be acquired), while the power consumption and the amount of heat generation are reduced. Moreover, in this case, similarly to the case of FIG. 2, a medical image with a better S/N can be acquired.

Furthermore, in a case where it is determined in step S21 that the temperature of the camera head 102 is not greater than the threshold THt and the velocity of movement of the camera head 102 is not greater than the threshold THv, the processing proceeds to step S23.

In step S23, the binning control unit 413 sets the respective operation modes of the image sensors 401 and 402 to the normal mode, and the processing returns to step S21. In this case, the resolution of a medical image can be increased (high-resolution medical image can be acquired). In other words, a medical image with higher resolution in blue and red can be acquired, in comparison to the case of the binning mode.

<Third Exemplary Configuration of Camera Head 102 and Third Exemplary Configuration Example of CCU 201>

Figure 8:
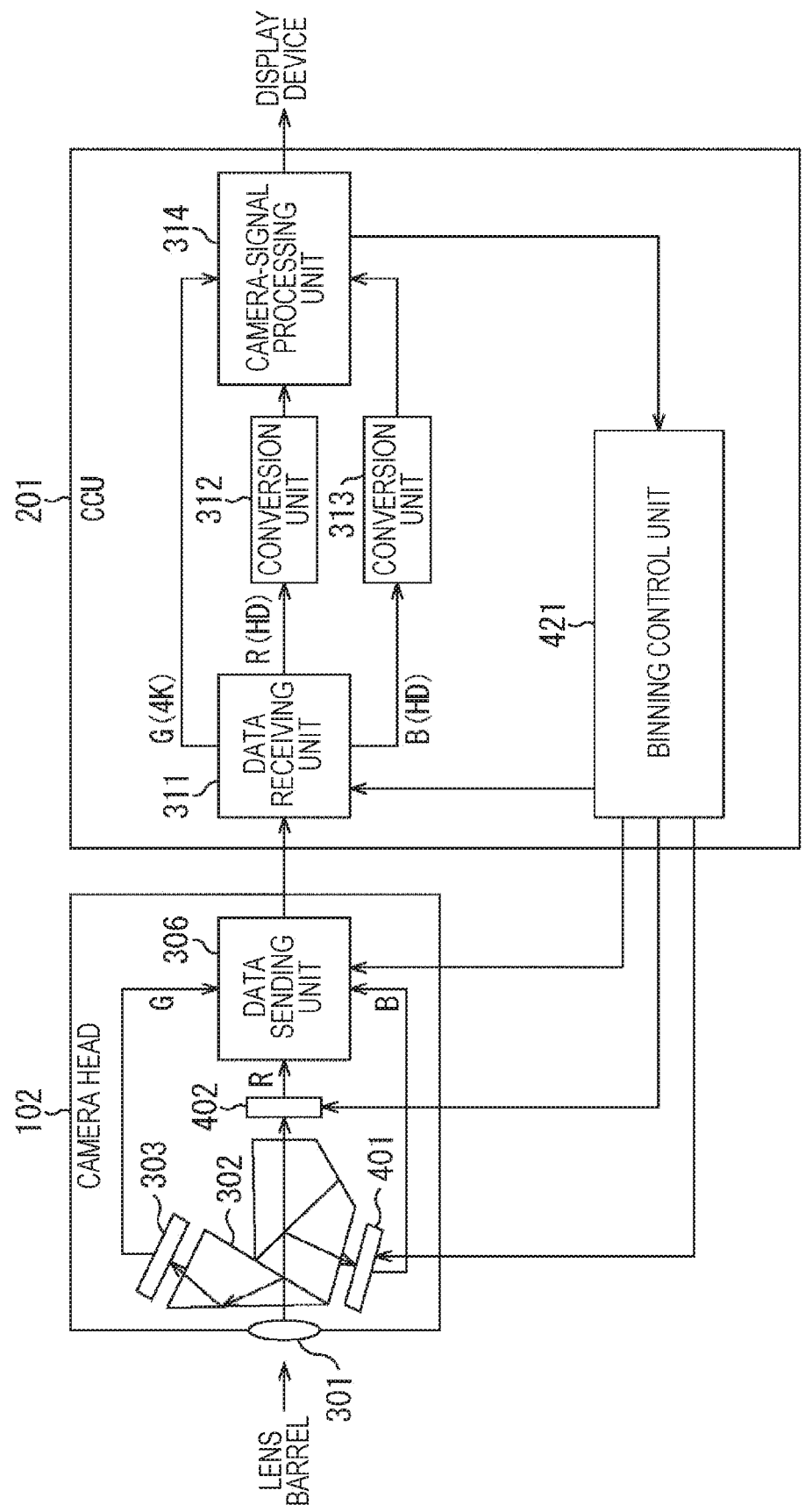
FIG. 8 is a block diagram of a third exemplary configuration of the camera head 102 and a third exemplary configuration of the CCU 201.

FIG. 8 is a block diagram of a third exemplary configuration of the camera head 102 and a third exemplary configuration of the CCU 201.

Note that in the figure, the same reference signs are given to parts corresponding to the case of FIG. 2 or FIG. 6, and the description of the corresponding parts will be appropriately omitted below.

In FIG. 8, the camera head 102 includes a lens 301, a prism 302, an image sensor 303, a data sending unit 306, and image sensors 401 and 402.

Thus, the camera head 102 of FIG. 8 is common to the case of FIG. 6 in that the lens 301, the prism 302, the image sensor 303, the data sending unit 306, and the image sensors 401 and 402 are included. The camera head 102 of FIG. 8, however, is different from the case of FIG. 6 in that a temperature sensor 411, a movement sensor 412, a binning control unit 413 are not provided.

Furthermore, in FIG. 8, the CCU 201 includes a data receiving unit 311, conversion units 312 and 313, a camera-signal processing unit 314, and a binning control unit 421.

Thus, the CCU 201 of FIG. 8 is common to the case of FIG. 2 in that the data receiving unit 311, the conversion units 312 and 313, and the camera-signal processing unit 314 are included. The CCU 201 of FIG. 8, however, is different from the case of FIG. 2 in that the binning control unit 421 is newly provided.

Note that in the CCU 201 of FIG. 8, the data receiving unit 311, the camera-signal processing unit 314, the NR unit 321, and the conversion units 322 and 323 of FIG. 5 can be provided instead of the data receiving unit 311, the conversion units 312 and 313, and the camera-signal processing unit 314.

The binning control unit 421 controls the respective operation modes of the image sensors 401 and 402, in accordance with a medical image (including a G image, an R image, and a B image to be used for generating a medical image) obtained by the camera-signal processing unit 314.

For example, the binning control unit 421 is capable of controlling each operation mode, in accordance with one or more of the amount of noise, the brightness, and the color of the medical image, and the degree of focusing for the medical image.

Specifically, for example, in a case where the amount of noise of the medical image is larger (in a case where the S/N is a threshold or less), the binning control unit 421 can set the operation mode to the binning mode, and in a case where the amount of noise of the medical image is smaller, the binning control unit 421 can set the operation mode to the normal mode. In a case where the amount of noise of the medical image is larger, the setting of the operation mode to the binning mode allows the camera-signal processing unit 314 to generate a medical image with less noise, with use of HD images as an R image and a B image with less noise respectively captured by the image sensors 401 and 402 in the binning mode.

Furthermore, for example, in a case where the brightness of the medical image is higher (in a case where the brightness is a threshold or greater), the binning control unit 421 can set the operation mode to the normal mode, and in a case where the brightness of the medical image is lower, the binning control unit 421 can set the operation mode to the binning mode. In a case where the brightness of the medical image is lower, the setting of the operation mode to the binning mode allows the camera-signal processing unit 314 to generate a medical image with much higher brightness, with use of HD images as an R image and a B image respectively captured by the image sensors 401 and 402 in the binning mode, the R image and the B image being higher in sensitivity to the light intensity.

Moreover, for example, in a case where the medical image is larger in the number of pixels of pixels dominated by red and (or) blue (in a case where the number of pixels is a threshold or greater), the binning control unit 421 can set the operation mode to the normal mode, and in a case where the medical image is smaller in the number of pixels of pixels dominated by red and blue, the binning control unit 421 can set the operation mode to the binning mode. In the case the where the number of pixels of pixels dominated by red and blue is larger, the setting of the operation mode to the normal mode allows the camera-signal processing unit 314 to generate a medical image in which a minute part is imaged clearly regarding red and blue, with use of 4K images as high-resolution R image and B image respectively captured by the image sensors 401 and 402 in the normal mode.

Furthermore, for example, in a case where the degree of focusing for the medical image is higher (e.g., in a case where the contrast (sharpness) of the medical image is a threshold or greater and it is estimated that the medical image is being focused), the binning control unit 421 can set the operation mode to the binning mode, and in a case where the degree of focusing for the medical image is lower, the binning control unit 421 can set the operation mode to the normal mode. In a case where the degree of focusing for the medical image is lower, that is, out of focus, the setting of the operation mode to the normal mode allows the camera-signal processing unit 314 to generate a high-resolution medical image, with use of 4K images as high-resolution R image and B image respectively captured by the image sensors 401 and 402 in the normal mode, whereby focus can be adjusted accurately with the generated medical image.

Besides, similarly to the binning control unit 413 of FIG. 6, the binning control unit 421 controls the data sending unit 306 and the data receiving unit 311, in accordance with the respective operation modes of the image sensors 401 and 402.

Note that in FIG. 8, the binning control unit 421 is provided in the CCU 201; however, the binning control unit 421 can be provided in the camera head 102. In a case where the binning control unit 421 is provided in the camera head 102, for example, a medical image (or G image, R image, and B image having used for generation of the medical image) can be supplied from the camera-signal processing unit 314 of the CCU 201 to the binning control unit 421 of the camera head 102, and the G image, the R image, and the B image can be supplied from the data sending unit 306 of the camera head 102 to the binning control unit 421 of the camera head 102.

Furthermore, similarly to the case of FIG. 6, each of the conversion units 312 and 313 in FIG. 8 performs upconversion in a case where the operation mode is in the binning mode, and does not perform upconversion in a case where the operation mode is in the normal mode.

Figure 9:
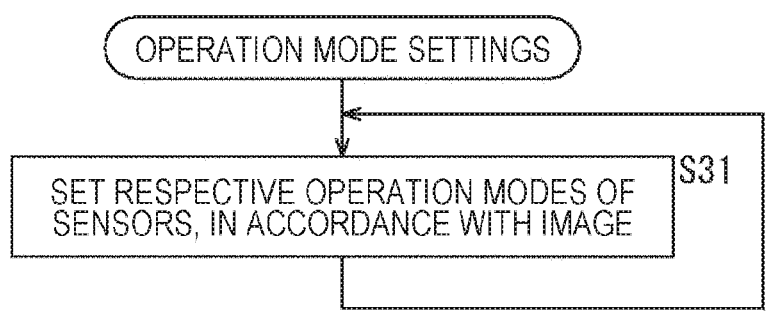
FIG. 9 is a flowchart for describing exemplary processing of operation mode settings performed by a binning control unit 421.

FIG. 9 is a flowchart for describing exemplary processing of the operation mode settings performed by the binning control unit 421 of FIG. 8.

In step S31, the binning control unit 413 repeats setting the respective operation modes of the image sensors 401 and 402 to the binning mode or the normal mode, in accordance with a medical image from the camera-signal processing unit 314.

Note that according to the present embodiment, a so-called three-chip type is adopted for the camera head 102, the three-chip type including the image sensor 303 that receives G light, the image sensor 304 or 401 that receives B light, and the image sensor 305 or 402 that receives R light. However, for example, a two-chip type or a four-chip type different from the three chips can be adopted as the configuration of the camera head 102.

Furthermore, at the camera head 102, B light and R light each are received as light different from G light; however, examples of the light different from the G light that can be received include visible light different from the B light and the R light, and infrared rays light different from visible light.

Moreover, the present technology is not only applicable to a case of displaying a two-dimensional (2D) image, but also applicable to a case of displaying a three-dimensional (3D) image.

Furthermore, in the present embodiment, there has been described a case where the present technology is applied to the endoscopic surgery system. The present technology, however, is applicable to various systems with which a medical image is captured, that is, for example, a microsurgery system, different from the endoscopic surgery system.

<Description of Computer with the Present Technology Applied>

Next, the series of processing of the CCU 201 described above can be performed by hardware or software. In a case where the series of processing is performed by software, a program included in the software is installed for example, on a computer of a microcomputer.

Figure 10:
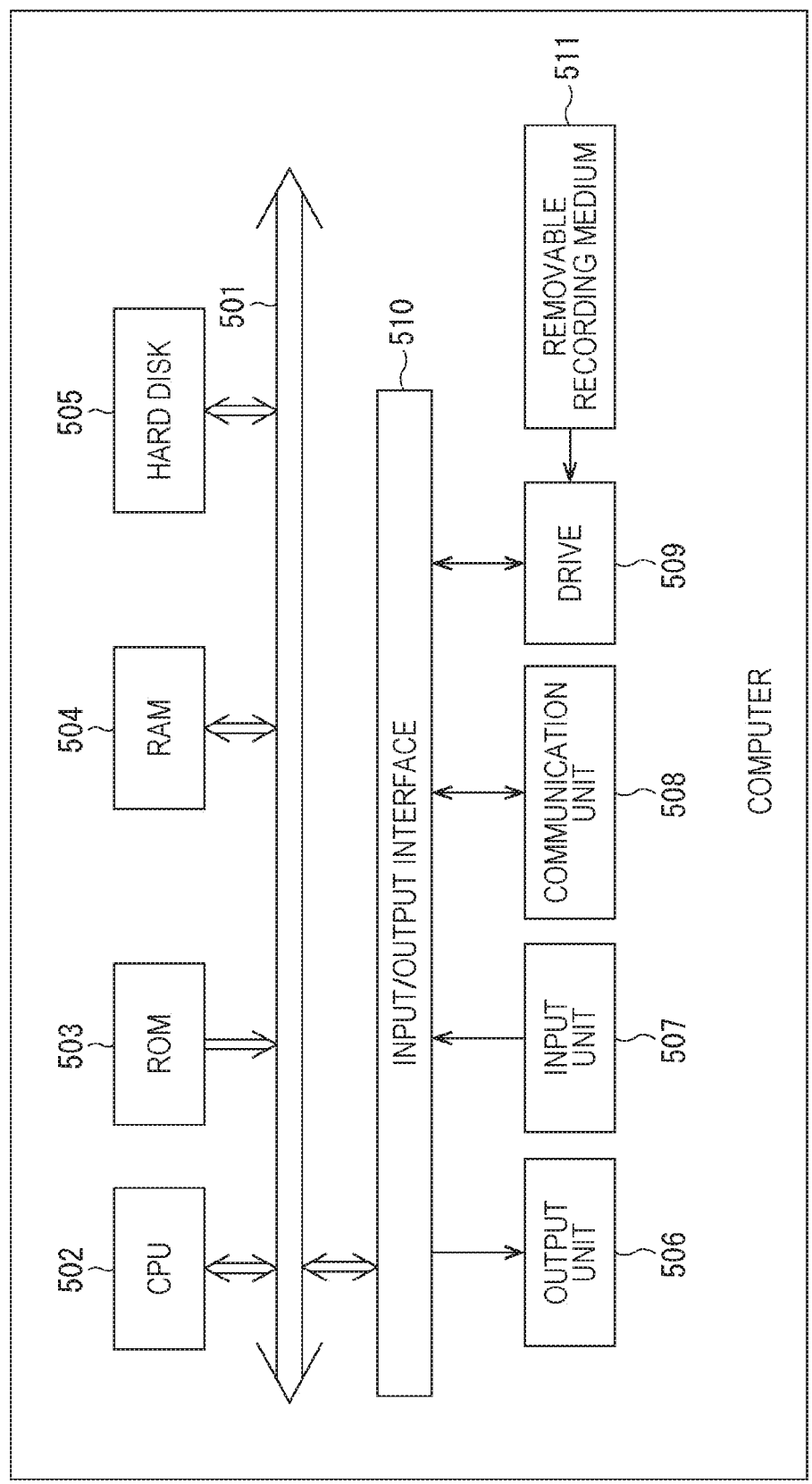
FIG. 10 is a block diagram of an exemplary configuration of one embodiment of a computer with the present technology is applied.

FIG. 10 is a block diagram of an exemplary configuration of one embodiment of a computer on which a program for execution of the series of the processing described above is installed.

The program can be pre-recorded in a hard disk 505 or a read only memory (ROM) 503 as a recording medium built in the computer.

Alternatively, the program can be prestored (pre-recorded) in a removable recording medium 511. Such a removable recording medium 511 can be provided as so-called package software. Here, examples of the removable recording medium 511 include a flexible disk, a compact disc read only memory (CD-ROM), a magneto optical (MO) disc, a digital versatile disc (DVD), a magnetic disk, and a semiconductor memory.

Note that in addition to installation on the computer from the removable recording medium 511 as described above, the program can be downloaded to the computer through a communication network or a broadcast network and can be installed in the built-in hard disk 505. In other words, for example, the program can be wirelessly transferred from a download site to the computer through an artificial satellite for digital satellite broadcasting, or can be wiredly transferred to the computer through a network such as a local area network (LAN) or the Internet.

The computer has a built-in central processing unit (CPU) 502, and an input/output interface 510 is connected to the CPU 502 through a bus 501.

When the user, for example, operates an input unit 507 and a command is input through the input/output interface 510, the CPU 502 executes the program stored in the read only memory (ROM) 503 according to the command. Alternatively, the program stored in the hard disk 505 is loaded into a random access memory (RAM) 504 and the CPU 502 executes the program.

As a result, the CPU 502 performs the processing following the above-described flowchart or the processing performed by the configuration of the above-described block diagram. Then, the CPU 502 causes an output unit 506 to output the result of the processing or a communication unit 508 to send the result of the processing, and further causes, for example, the hard disk 505 to record the result of the processing through, for example, the input/output interface 510, as necessary.

Note that the input unit 507 includes, for example, a keyboard, a mouse, and a microphone. Furthermore, the output unit 506 includes, for example, a liquid crystal display (LCD), and a speaker.

Here, in the present specification, the processing executed by the computer following the program does not necessarily need to be performed chronologically in the order described as the flowcharts. In other words, the processing executed by the computer following the program also includes processing executed in parallel or separately (e.g., parallel processing or processing with objects).

Moreover, in the present specification, the system means a collection of a plurality of constituent elements (e.g., device and module (component)), and it is unconcerned whether or not all the constituent elements are present in the same casing. Thus, a plurality of devices housed in separate casings and connected through a network, and one device having a plurality of modules housed in one casing are both systems.

Note that the embodiment of the present disclosure is not limited to the above-described embodiment, and various modifications can be made within the scope without departing from the gist of the present technology.

For example, each step described in the above-described flowcharts can be not only performed by one device, but also can be shared and performed by a plurality of devices.

Moreover, in a case where a plurality of pieces of processing is included in one step, the plurality of pieces of processing included in the one step can be not only performed by one device, but also can be shared and performed by a plurality of devices.

Furthermore, the effects described in the present specification are merely exemplified and are not intended to be limiting; thus, there may have additional effects.

Note that the present technology can adopt the following configurations.

<1>
An endoscope including
a camera head including:
a first sensor having pixels of a first number of pixels, the first sensor being configured to receive green (G) light that is light with a G wavelength band; and
a second sensor having pixels of a second number of pixels smaller than the first number of pixels, the second sensor being configured to receive light different from the G light.

<2>
The endoscope according to <1>,
in which a light-receiving face of the first sensor and a light-receiving face of the second sensor are equal in size.

<3>
The endoscope according to <1> or <2>
in which the second sensor is larger in pixel size than the first sensor.

<4>
The endoscope according to any of <1> to <3>,
in which the second sensor receives red (R) light that is light with an R wavelength band or blue (B) light that is light with a B wavelength band.

<5>
The endoscope according to any of <1> to <4>,
in which by using a first image having a pixel value corresponding to the G light, the first image being output from the first sensor, image processing is performed on a second image having a pixel value corresponding to the light different from the G light, the second image being output from the second sensor.

<6>
The endoscope according to <5>,
in which image processing is performed, by using the first image, on a part of the second image, the part being a threshold or greater in correlation with the first image.

<7>
The endoscope according to any of <1> to <6>,
in which by using a second image having a pixel value corresponding to the light different from the G light, the second image being output from the second sensor, image processing is performed on a first image having a pixel value corresponding to the G light, the first image being output from the first sensor.

<8>
The endoscope according to <7>,
in which image processing is performed, by using the second image, on a part of the first image, the part being a threshold or greater in correlation with the second image.

<9>
An endoscope including
a camera head including:
a first sensor having a predetermined number of pixels of pixels, the first sensor being configured to receive green (G) light that is light with a G wavelength band; and
a second sensor having the predetermined number of pixels of pixels, the second sensor being configured to receive light different from the G light,
in which the second sensor has a binning function of outputting an added value of pixel values of a plurality of pixels as a pixel value of one pixel, and outputs, with the binning function, a second image having a pixel value corresponding to the light different from the G light, the second image being smaller in the number of pixels than a first image having a pixel value corresponding to the G light, the first image being output from the first sensor.

<10>
The endoscope according to <9>, further includes:
a control unit configured to control an operation mode of the second sensor,
in which the second sensor has, as the operation mode, a binning mode for outputting, with the binning function, the second image being smaller in the number of pixels than the first image, and a normal mode for outputting the second image identical in the number of pixels to the first image.

<11>
The endoscope according to <10>,
in which the control unit controls the operation mode, in accordance with a state of the camera head.

<12>
The endoscope according to <11>,
in which the control unit controls the operation mode, in accordance with one or more of temperature and movement of the camera head.

<13>
The endoscope according to <10>,
in which the control unit controls the operation mode, in accordance with the first image and the second image.

<14>
The endoscope according to <13>,
in which the control unit controls the operation mode, in accordance with one or more of an amount of noise, brightness, color, and a degree of focusing for the first image and the second image.

<15>
The endoscope according to any of <9> to <14>,
in which the second sensor receives red (R) light that is light with an R wavelength band or blue (B) light that is light with a B wavelength band.

<16>
The endoscope according to any of <9> to <15>,
in which image processing is performed on the second image, by using the first image.

<17>

The endoscope according to <16>, in which image processing is performed, by using the first image, on a part of the second image, the part being a threshold or greater in correlation with the first image.

<18>

The endoscope according to any of <9> to <17>, in which image processing is performed on the first image, by using the second image.

<19>

The endoscope according to <18>, in which image processing is performed, by using the second image, on a part of the first image, the part being a threshold or greater in correlation with the second image.

REFERENCE SIGNS LIST

10 Endoscope
100 Endoscope
101 Lens barrel
102 Camera head
110 Surgical tools
111 Pneumoperitoneum tube
112 Energy treatment instrument
120 Support arm device
131 Operator
132 Patient
133 Patient bed
200 Cart
201 CCU
202 Display device
203 Light source device
204 Input device
205 Treatment-instrument control device
206 Pneumoperitoneum device
207 Recorder
208 Printer
301 Lens
302 Prism
303 to 305 Image sensor
306 Data sending unit
311 Data receiving unit
312, 312 Conversion unit
314 Camera-signal processing unit
321 NR unit
322, 323 Conversion unit
401, 402 Image sensor
411 Temperature sensor
412 Movement sensor
413, 421 Binning control unit
501 Bus
502 CPU
503 ROM
504 RAM
505 Hard disk
506 Output unit
507 Input unit
508 Communication unit
509 Drive
510 Input/output interface
511 Removable recording medium

The invention claimed is:

1. An endoscope comprising:
a camera head including
a first sensor having a first number of pixels, the first sensor being configured to receive green (G) light that is light with a G wavelength band;
a second sensor having a second number of pixels smaller than the first number of pixels, the second sensor being configured to receive red (R) light that is light with a R wavelength hand; and
a third sensor having a third number of pixels smaller than the first number of pixels, the third sensor being configured to receive blue (B) light that is light with a B wavelength band, wherein
by using a first image having a pixel value corresponding to the G light, the first image being output from the first sensor, image processing is performed on at least one of:
a part of a second image having a pixel value corresponding to the R light, the second image being output from the second sensor, the part of the second image having a first correlation with the first image, the first correlation being equal to or greater than a threshold, and
a part of a third image having a pixel value corresponding to the B light, the third image being output from the third sensor, the part of the third image having a second correlation with the first image, the second correlation being equal to or greater than the threshold.

2. The endoscope according to claim 1, wherein a light-receiving face of the first sensor, a light-receiving face of the second sensor, and a light-receiving face of the third sensor are equal in size.

3. The endoscope according to claim 1, wherein the second sensor and the third sensor are larger in pixel size than the first sensor.

4. The endoscope according to claim 1, wherein the second number and the third number are the same.

5. An endoscope comprising:
a camera head including
a first sensor having a first number of pixels, the first sensor being configured to receive green (G) light that is light with a G wavelength band;
a second sensor having a second number of pixels smaller than the first number of pixels, the second sensor being configured to receive red (Might that is light with a R wavelength band; and
a third sensor having a third number of pixels smaller than the first number of pixels, the third sensor being configured to receive blue (B) light that is light with a B wavelength band, wherein
by using a second image having a pixel value corresponding to the R light, the second image being output from the second sensor, image processing is performed on a part of a first image having a pixel value corresponding to the G light, the first image being output from the first sensor, the part of the first image having a correlation with the second image, the correlation being equal to or greater than a threshold.

6. The endoscope according to claim 5, wherein a light-receiving face of the first sensor, a light-receiving face of the second sensor, and a light-receiving face of the third sensor are equal in size.

7. The endoscope according to claim 5, wherein the second sensor and the third sensor are larger in pixel size than the first sensor.

8. The endoscope according to claim 5, wherein the second number and the third number are the same.

9. An endoscope comprising:
a camera head including
- a first sensor having a first number of pixels, the first sensor being configured to receive green (G) light that is light with a G wavelength band;
- a second sensor having a second number of pixels smaller than the first number of pixels, the second sensor being configured to receive red (R) light that is light with a R wavelength band; and
- a third sensor having a third number of pixels smaller than the first number of pixels, the third sensor being configured to receive blue (B) light that is light with a B wavelength band, wherein by using a third image having a pixel value corresponding to the B light, the third image being output from the third sensor, image processing is performed on a part of a first image having a pixel value corresponding to the G light, the first image being output from the first sensor, the part of the first image having a correlation with the third image, the correlation being equal to or greater than a threshold.

10. The endoscope according to claim 9,
wherein a light-receiving face of the first sensor, a light-receiving face of the second sensor, and a light-receiving face of the third sensor are equal in size.

11. The endoscope according to claim 9,
wherein the second sensor and the third sensor are larger in pixel size than the first sensor.

12. The endoscope according to claim 9,
wherein the second number and the third number are the same.

* * * * *